(12) United States Patent
Chopra (10) Patent No.: US 6,960,357 B2
(45) Date of Patent: Nov. 1, 2005

(54) CHEMICAL DELIVERY DEVICE

(75) Inventor: Sham Chopra, Brampton (CA)

(73) Assignee: Mistral Pharma Inc., Quebec (CA)

( * ) Notice: Subject to any disclaimer, the term of this patent is extended or adjusted under 35 U.S.C. 154(b) by 177 days.

(21) Appl. No.: 10/085,234

(22) Filed: Feb. 28, 2002

(65) Prior Publication Data

US 2003/0003151 A1 Jan. 2, 2003

Related U.S. Application Data

(60) Provisional application No. 60/293,701, filed on May 25, 2001.

(51) Int. Cl.[7] .............................. A61K 9/22; A61K 9/32; A61K 9/36
(52) U.S. Cl. ....................... 424/480; 424/468; 424/474; 424/475; 424/482
(58) Field of Search ................................ 424/463, 468, 424/474, 475, 480, 482, 490, 493, 494, 495, 497, 472, 464, 479, 489, 465, 400; 264/109

(56) References Cited

U.S. PATENT DOCUMENTS

| | | |
|---|---|---|
| 3,113,076 A | 12/1963 | Jacobs |
| 3,851,648 A | 12/1974 | Brooke |
| 3,924,622 A | 12/1975 | Brooke |
| 4,557,925 A | 12/1985 | Lindahl et al. |
| 4,663,147 A | 5/1987 | DePrince |
| 4,687,660 A | 8/1987 | Baker et al. |
| 4,783,337 A | 11/1988 | Wong |
| 4,803,076 A | 2/1989 | Ranade |
| 4,816,262 A | 3/1989 | McMullen |
| 4,824,678 A | 4/1989 | Lindahl et al. |
| 4,839,177 A * | 6/1989 | Colombo et al. ........... 424/482 |
| 5,178,868 A | 1/1993 | Malmqvist-Granlund et al. |
| 5,342,627 A | 8/1994 | Chopra et al. |
| 5,422,123 A * | 6/1995 | Conte et al. ................. 424/479 |
| 5,922,342 A | 7/1999 | Shah et al. |
| 6,110,500 A | 8/2000 | Kim |
| 6,264,985 B1 | 7/2001 | Cremer |
| 2001/0038853 A1 | 11/2001 | Kendrup et al. |

* cited by examiner

*Primary Examiner*—James M. Spear
(74) *Attorney, Agent, or Firm*—Fox Rothschild LLP (57) ABSTRACT

The invention provides a controlled release dissolution and diffusion devices which can deliver an active ingredient at a constant or controlled-variable rate comprising an active ingredient and dissolution modifiers and/or an insoluble matrix. The compressed core is coated, except for at least one exposed face, with a coating containing an insoluble polymer or a mixture of an insoluble polymer and pore-forming elements said pore-forming elements having a dissolution rate slower that the release rate so that the pore formation is completed after release of the active ingredients and the residual inert structures disintegrate.

27 Claims, 6 Drawing Sheets

CHEMICAL DELIVERY DEVICE

REFERENCE TO PREVIOUS APPLICATIONS

This application claims priority to U.S. Provisional Patent Application Ser. No. 60/293,701 filed May 25, 2001.

FIELD OF THE INVENTION

The present invention relates to controlled release chemical delivery devices, and more particularly to a controlled release drug delivery device, with a geometrically shaped body coated with a mixture of an insoluble polymer, optionally containing water-soluble pore-forming material(s) said pore-forming material(s) having a dissolution rate slower that the release rate so that the pore formation is completed after release of the active ingredients and the residual inert structures disintegrate.

BACKGROUND OF THE INVENTION

Effective drug therapy generally requires maintained drug levels in the blood stream for extended periods of time. Standard tablets, however, generally disintegrate quickly and release all the active components over a relatively short period of time. With these dosage forms drug levels are maintained by administering the tablets several times a day. This is inconvenient and frequently leads to poorer patient compliance. Thus it is desirable to identify drug delivery systems which will produce constant drug levels in the blood for extended time periods. It is thought that to obtain a constant drug level in the blood a drug delivery system must release the drug at a constant rate. To achieve this constant rate, several mechanisms including osmosis, diffusion and dissolution, and dosage form modifications have been investigated, for example as described in Ho-Wah Hui et al., Chapter 9 in "Controlled Drug Delivery": Fundamentals and Applications ($2^{nd}$ Ed.), Marcel Dekker, New York, 1987. There remains, however, a clear and continuing need for simple inexpensive dosage forms which efficiently and reliably deliver active compounds over extended time periods.

Drug delivery systems frequently include passive impermeable coatings which surround a core composition containing the active drug substance and excipients. This coating frequently plays an important role in maintaining the structural integrity of the device during the drug release period. If the impermeable coating does not dissolve or disintegrate prior to passage through the gastrointestinal system, a "ghost" residue will remain which can be uncomfortable or undesirable to void. Furthermore, passage of these residual coatings through the GI tract potentially can damage the intestinal mucosa.

Attempts have been made to achieve constant rates of drug release by controlling the surface area of tablets. Examples of such attempts are described in Stephenson et al. (UK Patent No. 1,022,171), Reid (U.S. Pat. No. 3,279,995) and DePrince (U.S. Pat. No. 4,663,147). However, such systems have not been completely successful usually either due to improper design of the system or due to a lack of appropriate and available manufacturing technology.

Another approach has been to coat the active component with impermeable coatings which limit access of the fluid media to the active component and slow dissolution of the core. Staniforth (U.S. Pat. No. 5,004,614) employs a coated tablet containing holes in the coating to limit contact with the surrounding medium. Both dissolution and diffusion process can be exploited to attempt to regulate drug release from delivery devices. Ranade (U.S. Pat. No. 4,803,076) has disclosed a dissolution and diffusion device for the controlled release of a substance into a fluid media at a substantially constant rate wherein the substance is contained in a shape substantially that of a truncated cone in which the sides and base (but not the top) of the cone are coated with an impermeable wall or coating. A related design was disclosed by Cremer (U.S. Pat. No. 6,264,985). McMullen (U.S. Pat. No. 4,816,262) describes a controlled release tablet which includes a solid core having a hydrophilic releasable agent. The core has a central hole and is coated on all faces except that formed by the central hole. The thickness gradually increases from the central hole to the outer border and forms a concave disk containing a hydrophilic releasable agent. Chopra (U.S. Pat. No. 5,342,627) describes a tablet shaped core in which the thickness decreases from the center of the tablet to the periphery and the exposed surface from which release occurs is a cylindrical band around the outer perimeter of the tablet. Kim (U.S. Pat. No. 6,110,500) has disclosed a tablet for controlled release of an active ingredient from a core having a donut-like configuration with a cylindrical hole extending through the center of the core. The core comprises a releasable substance and at least one hydrophilic, water-soluble polymeric carrier. These hydrophilic polymeric carriers are swellable and/or erodable. Swelling of the polymer, however, can deform the controlled release device and alter the release rates. The core is coated with a hydrophobic water insoluble material except the area defined by the cylindrical hole through the core. Cremer (U.S. Pat. No. 5,853,760) teaches a device for the controlled release of active substances into fluid media from an active substance-containing matrix, the active substance releasing surfaces of which are, at least partially, covered by an erodible solid. The delivery characteristics depend on the surfaces coated and the thickness and geometry of the coating which erodes over the delivery period to expose additional surfaces of the matrix to the fluid medium. Shah and Britten (U.S. Pat. No. 5,922,342) disclose a controlled release composition with a compressed core having two parallel planar surfaces containing at least 90% of a non-disintegrating therapeutic agent(s) and optionally containing 0–10% of non-disintegrating ingredients that are conventional in tablet making such as binders, lubricants, compression aids, flow aids and the like. The device allows zero-order release of a drug throughout the delivery period. The core is free of materials that can cause swelling or disintegrate. A seal coating consisting of a film of impermeable material surrounds the core except the two parallel planar surfaces (i.e. on all the later surfaces. The seal coating serves to protect the lateral surfaces of the core.

The osmotically driven systems (e.g. U.S. Pat. No. 4,111,202) release the drug at a constant rate for as long as the concentration of the osmotic agent in the system is at the saturation point. When the concentration of the osmotic agent falls below the saturation point, the release rate declines parabolically towards zero as described in F. Theeuwes et al. Elementary Osmotic Pump for indomethacin, J. Pharm. Sci., 72, 253, (1983).

Dissolution-controlled and diffusion controlled devices consist of a pharmaceutical agent mixed with inert ingredients compressed into tablets. A dissolution-controlled device contains a shaped core, optionally partially coated with an insoluble polymeric coating, in which the exposed portion of the core dissolves into or is eroded by the surrounding media whereby the active compound is released into the media. The shaped core contains the active ingredient optionally combined with release-modifying agents, buffers and binders. A dissolution device is suitable for formulating hydrophobic and hydrophilic compounds whereas a diffusion device is especially suited to deliver hydrophilic compounds. A diffusion-controlled device contains a pharmaceutical agent uniformly distributed in an insoluble porous polymeric matrix. The insoluble matrix is present throughout the delivery period and the dimensions of the device remain constant. As the drug becomes depleted in proximity of the exposed surface, the release rate also becomes a function of the diffusion path length through the insoluble matrix through which the remaining drug must diffuse to reach the exposed surface in contact with the dissolution media.

Some therapeutic regimens require administering a varying quantity of the active substance. Attempts have been made to design dosage forms which produce variable release rates or pulsatile release but these have not been reliable or cost effective since they frequently possess complex architectures which are difficult to fabricate and are structurally weak. For example, Chopra (U.S. Pat. No. 5,342,627) teaches that "the geometrical profile of the cavity and core of the diffusion device may be such that 'pulses' of the active substance are release at predetermined points in the total dissolution time. Thus, the profile of the cavity 'walls' may be varied to provide pre-determined changes in the surface are so as to provide pulses of activity." There is, however, no explanation of geometries which will produce nonlinear release nor does the geometry of the device allow for ready modification.

The release rate of a chemical from a compressed soluble disc in a dissolution-controlled device, dm/dt, can be expressed as:

$$\frac{dm}{dt} = AC\frac{dx}{dt} \quad \text{(Equation 1)}$$

where: A is the surface area;
C is the concentration of the chemical; and
dx/dt is the mass erosion rate.

Equation (1) predicts that the release rate will be proportional to the exposed surface area if the mass erosion rate is constant and the chemical substance is uniformly distributed throughout the core of the tablet. In reality, however, the rate of dissolution is not a simple function of surface area alone, rather it is a complex function of changing size and the shape of the disc itself, as well as fluid dynamics of the adjacent solvent layer as described in F. J. Rippie and J. R. Johnson, *Regulation of Dissolution Rate by Pellet Geometry, J. Pharm. Sci.*, 58, 428 (1969). Nevertheless, if the device is designed to provide a constant surface area over a substantial portion of the delivery period, a constant dissolution rate can be expected. (D. Brooke and R. J. Washkuhn, *Zero-order Drug Delivery Systems: Theory and Preliminary Testing, J. Pharm. Sci.*, 1979 66:159).

In the diffusion mechanism, the release of chemical from a solid matrix by diffusion can be represented by Equation 2:

$$\frac{dq}{dt} = -DA\frac{dc}{dr} \quad \text{(Equation 2)}$$

where q is the mass of chemical being transferred;
t is the time;
c is the chemical concentration;
r is the diffusion path length;
A is the area for the mass transport; and,
D the diffusion coefficient of the chemical.

According to the above equation, the chemical release rate decreases as the diffusion path length r increases. Since r cannot be kept constant, a constant release rate can be maintained by increasing the concentration of active compound by exposing greater surface area to compensate for the increase in diffusion distance through the matrix.

Existing devices have features that limit their applicability and practical production of effective controlled release agents has proven difficult. Devices which do not provide for adequate quantities of a dissolution regulator have limited flexibility to optimize the delivery rate. Water-soluble compounds will be released too rapidly when present in very high concentration in dissolution devices. Devices which do not provide for insoluble modifiers are incapable of functioning as diffusion devices which are desirable when delivering hydrophobic compounds. If improperly designed, the release rate from controlled release devices may vary over the release period. Osmotic devices have a lag time until the desired release rate is achieved whereas the present devices begin to deliver the active chemical upon contact with the fluid medium. The release from osmotic systems also decreases suddenly once the osmotic regulant is depleted from the device leaving residual active compound in the device. Diffusion-controlled devices in which the active compound must diffuse through an insoluble matrix may have a lag time or slow release rate and be voided intact before the complete release of the active ingredient.

Premature separation of the impermeable coating from the core can cause "dose dumping" as the uncoated core disintegrates Impermeable coatings in existing devices have no reliable disintegration mechanism which can lead to evacuation of the intact coating or release device. Furthermore the amount of active substance which can be accommodated by these known devices is often limited by practical difficulties scaling the size and geometry of these architecturally complex devices. The rate of release from devices with a swellable and/or erodible polymer decrease in the later stages of drug release whereas dissolution devices afford constant release throughout the delivery period. The release rate from swellable cores also can be erratic due to the hydrodynamic conditions in the gastrointestinal tract as the swellable polymers are easily abraded. Release from an erodible matrix decreases as the surface area of the erodible surface decreases. Diffusion devices often exhibit non-zero order release as the diffusion path between the residual active substance and the fluid medium increases. A variety of geometrical designs have been suggested to overcome these problems; however, implementing these designs has often been problematical.

The release rate from these devices is dependent on a variety of factors. The geometrical shape of the matrix is an important parameter. Other factors include, but not limited to, the specific properties of the substances used, e.g., molecular mass, solubility, swelling temperature and glass transition temperature of the components of the device. When the release requires diffusion through a matrix, the main parameters include the size of the surface, the matrix volume, the diffusion coefficient, the concentration and solubility of the active substance in the matrix, the porosity and tortuosity of the matrix, and the diffusion resistance between the matrix and the fluid medium.

Many controlled release delivery devices incorporate polymeric coatings that are essentially water insoluble and consequently have low permeability to both water and the active component in the device. Depending upon the physical principles utilized to control delivery of the active ingredient, these coatings may be modified to alter their permeability. Several approaches to controlled drug delivery devices utilize a core containing the active ingredient with an impermeable polymeric coat containing particulate pore-forming materials which are soluble in water or in gastrointestinal fluids. Lindahl and Erlandsson (U.S. Pat. Nos. 4,557,925; 4,629,619 and 4,629,620) utilize pore-forming materials that dissolve or leach out of the coating which creates paths or channels allowing ingress of the surrounding fluids which dissolve the active compound and produce saturated solutions of the active compound in the core which subsequently egress through the same channels. The release rates in these relatively simple devices are predominantly a function of the time required for dissolution of the particles and the size and density of the channels. These variables depend on the solubility and particle size of the pore-forming material and the concentration in the impermeable coat. Berliner and Nacht (U.S. Pat. No. 5,849,327) disclosed delivery devices in which the pore-forming materials are degraded by colon specific bacteria resulting in release of the active ingredient in the colon. Lindahl and Ekland (U.S. Pat. No. 4,824,678) describe delivery devices utilizing this principle by incorporating the active ingredient in the core and in the pore-creating particles which produces a burst of active ingredient as the pores are formed.

Osmotic delivery devices also have incorporated pore-forming materials within impermeable or semipermeable polymeric coatings to provide channels for osmotic pumping of the contents into the external medium. For example, Haslam and Rork (U.S. Pat. No. 4,886,668) describe an osmotic device wherein pore-forming materials are incorporated with a semipermeable coating. Ingress of water occurs through the semipermeable coating and dissolution or leaching of the pore-forming materials provides egress channels for the concentrated solution of active component formed in the core.

Regardless of the physical principles underlying the design and operation of the delivery device, the pore-forming compounds are incorporated to provide a pathway to move fluids through the impermeable polymeric coating.

There remains a need for effective and adaptable systems for controlled release of active chemicals with improved performance. The devices in the present invention can be readily scaled to different proportions that will accommodate differing quantities of the active chemical and which, therefore, have the capacity for longer release periods. With the present system the core is slow dissolving, which means that "dose dumping" is not as prevalent as in other chemical delivery systems, and there is minimal effect of hydrodynamic conditions prevailing in the stomach as only the peripheral face of the core is exposed. The present system also provides a reliable and predictable means to insure disintegration of the insoluble impermeable coating to avoid elimination of the intact device. Furthermore the rate of disintegration of the coating can be manipulated by adjusting the size, density and composition of the pore-forming materials.

BRIEF DESCRIPTION OF THE DRAWINGS

Other objects and features of the present invention will become apparent from the following detailed description considered in connection with the accompanying drawing which discloses several embodiments of the present invention. It should be understood, however, that the drawing is designed for the purpose of illustration only and not as a definition of the limits of the invention.

DETAILED DESCRIPTION OF THE INVENTION

Although many approaches have been taken to design controlled release systems which release a pharmaceutical agent according to a predetermined release profile, there remains an unfilled need for simple and reliable dissolution- and diffusion-controlled delivery devices that are manufactured with relative ease and acceptable cost. One embodiment of the present invention is a new simple chemical delivery device. The delivery device produces linear (zero-order) kinetics for releasing a chemical compound over a desired period. The delivery device comprises a geometrically shaped core with at least one planar release face exposed to the fluid medium, at least one chemical compound and at least one dissolution regulator dispersed within the core. The core is surrounded by an insoluble polymer coating and water-soluble pore-forming material(s) that leach out of the coat and that introduce mechanical instability and allow the coat to disintegrate after release of the active compound is complete. The disintegration rate of this coating can be manipulated by changing the concentration and/or size of pore-forming material(s), the water-solubility of the material(s) and the thickness and composition of the coating. Another embodiment of the present invention is a chemical delivery device which can independently release more than one chemical ingredient. In the present invention this can be achieved by incorporating one substance into the shaped core and a second substance into the coating which erodes at a substantially slower rate than the core resulting in a release rate different from the drug in the core. Alternatively the core can be comprised of multiple layers with each compound in one of the layers or two compounds can be mixed within a single shaped core. In this embodiment of the invention the relative surface area of the exposed face of each layer will determine the relative release rate for the chemical compound contained therein.

The chemical compounds used in the present invention may include, but are not limited to, therapeutically active compounds for human and veterinary applications, pesticides useful in agriculture such as insecticides and fungicides, disinfectants and biocides to control growth of undesired organisms, active compounds used in water treatments in swimming pools and toilets and any other application in which the release of a chemical at a controlled rate is required.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "comprising", "including" and "having" are used interchangeably. Furthermore, a compound "selected from the group consisting of" refers to one or more of the compounds in the list that follows, including mixtures (i.e., combinations) of two or more of the compounds.

The terms "controlled-release", "sustained-release" and "slow-release" are to be considered as synonyms in the context of the present invention. The term "controlled release", as used herein means that the release of the therapeutically active agent occurs such that blood levels are maintained within a desired therapeutic range over an extended period of time, e.g., at least about 6 and preferably from about 12 to about 24 hours.

The term "core" as used herein can be interchanged with the term "body", and is used to describe the part of the tablet that contains the active ingredient(s) and excipients and that is covered by a slowly dissolving or disintegrating coat, preferably a coat that dissolves or disintegrates only after the active ingredient is released from the core. The term "exposed surface" or "release surface" as used herein means the uncoated surfaces of the core in direct contact with the external fluid medium. One embodiment of the invention is a shaped core covered by a coating comprising soluble and insoluble components whereby the soluble components can leach out or dissolve and render the insoluble coating porous and structurally weak allowing it to disintegrate after the all the active compound is released but before the tablet is evacuated.

The term "dissolution regulator", "release modifying agent" or "soluble diluents" as used herein means a chemical compound included in the core to surround the particles of the active compound and modify its inherent dissolution rate.

The term "dissolution-controlled" as used herein means the components of the shaped-core erode or dissolve away from the original exposed surface of the device. There is no limitation on the mechanism or physical processes whereby the erosion occurs.

The term "diffusion-controlled" as used herein means the active compound(s) is(are) disposed in an insoluble matrix and the shape and dimensions of the matrix remain substantially unchanged during the delivery period. In a diffusion-controlled device the "dissolution front" or "dissolution surface", where active compound is released into the fluid medium, is within the insoluble matrix and only coincident with the exposed surface at the initial point in the release profile. During the release period the dissolution front moves away from the exposed face of the matrix and the active substance released from the dissolution front within the insoluble matrix must diffuse through pores of the insoluble matrix to reach the surface, i.e., "release front", exposed to the fluid medium.

The term "diffusion path length" as used herein refers to the distance between the dissolution surface and the surface exposed to the external fluid media through which the active compound must diffuse.

The term "erosion" or "eroded" as used herein denotes a process whereby mass is removed from the exposed faces by mechanical degradation (e.g. surface disintegration) or by dissolution of the dissolution regulator or by a more complex process including, but not limited to a chemical reaction, e.g. hydrolysis, of matrix components.

The term "pore-forming material(s)", "pore-forming element(s)" or "pore former(s)" as used herein refers to water soluble materials which are embedded throughout the insoluble coating and which dissolve, erode or leach out of the coating, The pore-forming materials can be in solid or liquid form embedded in the coat. These pores do not alter the drug release rate and are designed to form after the drug release period is substantially completed and allow disintegration of the device and coating prior to passage put of the colon.

The term "substantially constant" as used herein means that release of the active ingredient does not deviate by more than ±20% from the theoretical release rate and preferably does not deviate by more than ±10% from the theoretical release rate. The term "delivery period" as used herein refers to time period expected for complete release of the active compound. A "substantial portion of the delivery period" as used herein means that 70–80% of the active ingredient has been delivered. It is understood that this can vary widely with the precise application and the manufacturing conditions. Devices for oral delivery of a pharmaceutical compound will typically release within 24 hours to avoid evacuation of the device with unreleased active ingredient remaining therein. Agricultural applications may require significantly longer release periods for the active compound. Biocidal and disinfectant applications will preferably have very slow release rates to maximize the effective lifetime of the device. Manufacturing variables such as compression force will effect the dissolution times of the core and the useful delivery period; and, these parameters must be optimized for a specific application and specific components.

Figure 1A:
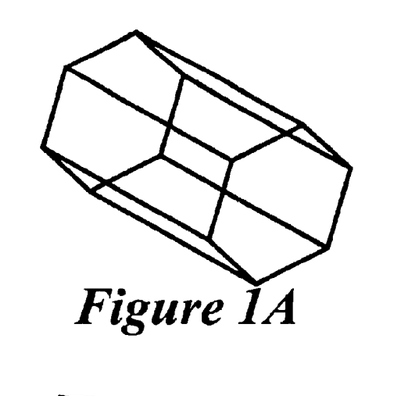
FIGS. 1A–G shows different embodiments of a geometrically shaped core of the present invention that maintain a constant surface area throughout the delivery process.
Figure 1B:
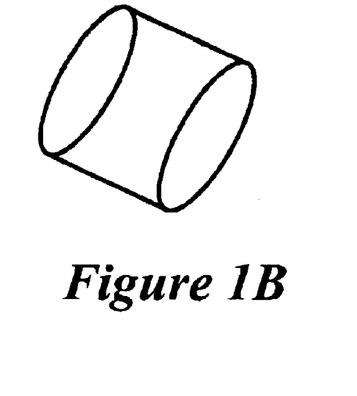
Figure 1C:
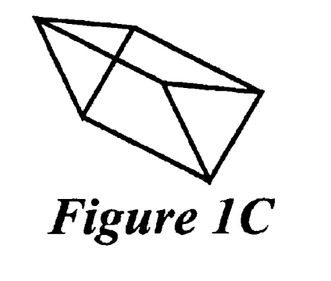
Figure 1D:
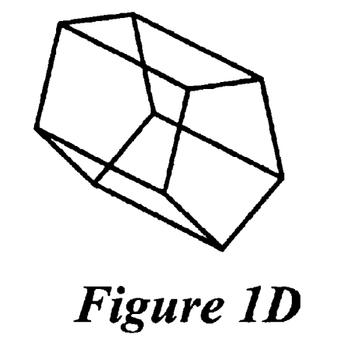
Figure 1E:
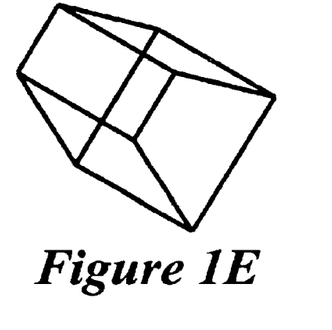
Figure 1F:
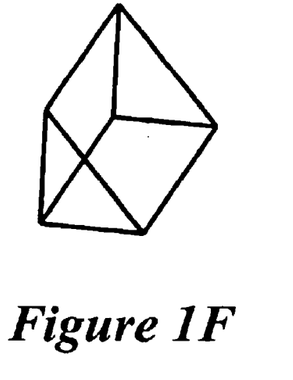
Figure 1G:
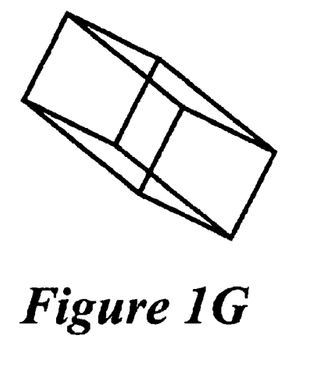
Figure 2A:
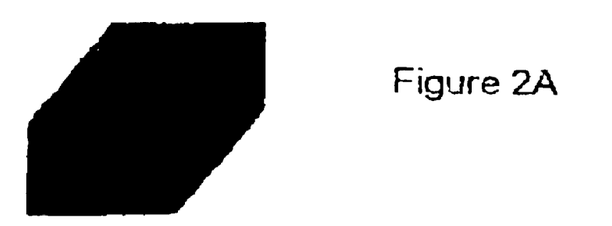
FIG. 2A illustrates one embodiment of the core that is rectangular.
Figure 2B:
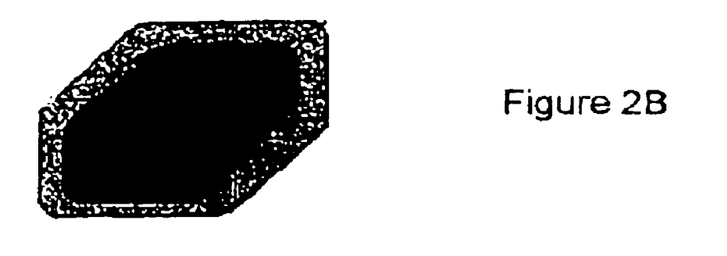
FIGS. 2B–D show the coated core of FIG. 2A at varying stages of chemical release.
Figure 2C:
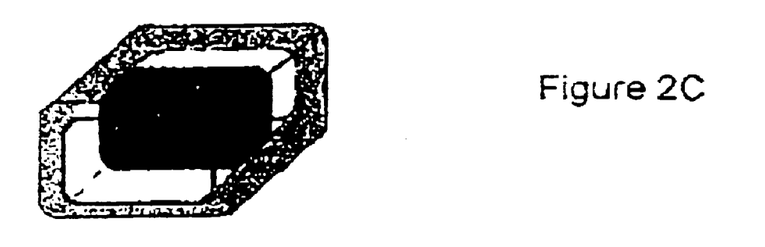
Figure 2D:
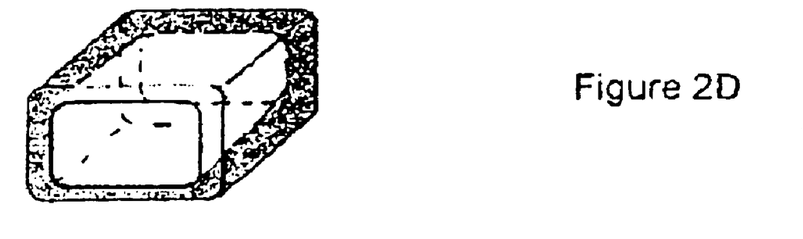
Figure 2E:
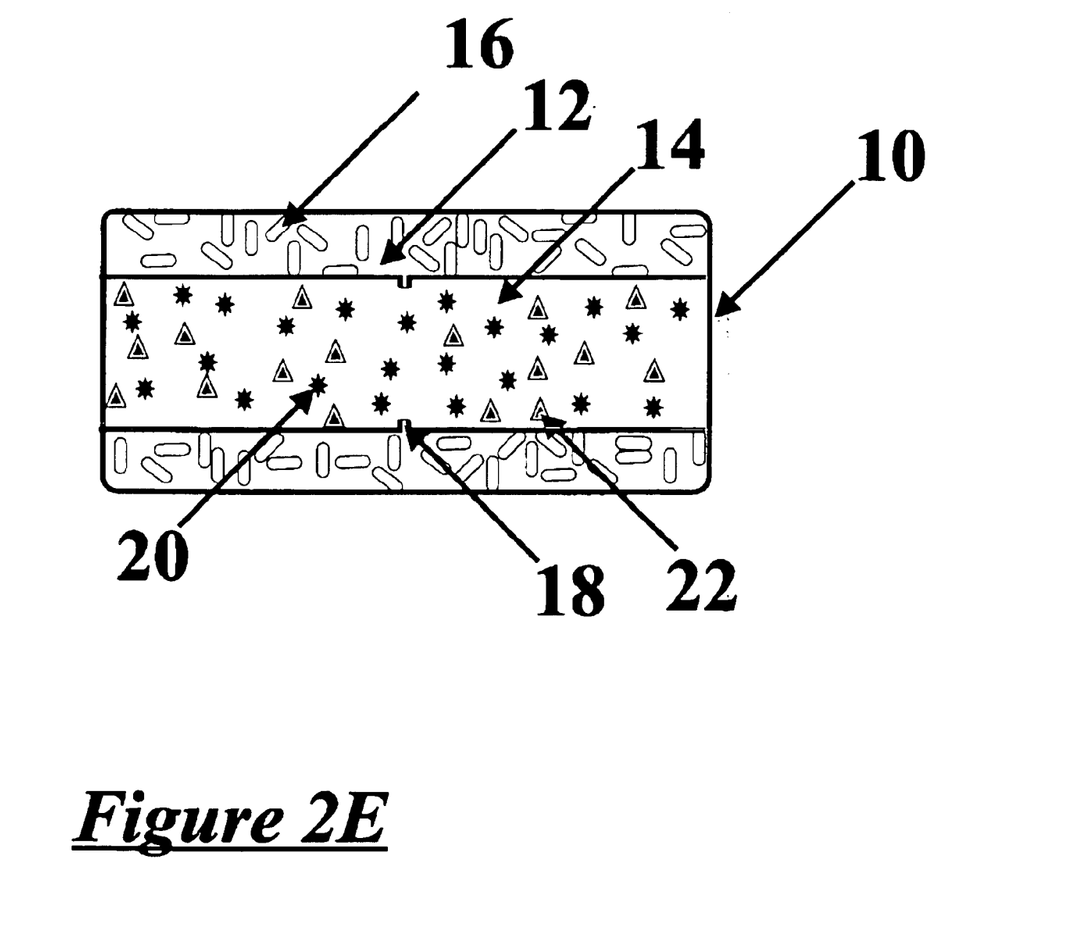
FIG. 2E is a cross-section view of a typical dissolution delivery device containing pore-forming elements in the coat.

The delivery device of the present invention can be based on the dissolution mechanism. As shown in FIGS. 1A–G and 2A–E, the device preferably consists of a geometrically shaped core 10, preferably a rectangular, cubical or cylindrical shaped core. The core 10 contains a uniformly dispersed chemical compound or compounds including an active ingredient 20 and a dissolution regulator 22; preferably the uniformly dispersed active ingredients are therapeutically active compound(s). The compressed core can optionally be scored 18 to secure the slowly dissolving or disintegrating coating to the compressed core. A slowly dissolving or disintegrating coat 12 optionally containing pore-forming material 16 surrounds all but at least one face 14 of the core as shown in FIG. 2B. As the two exposed surfaces erode the two faces recede inwards until the core 10 is dissolved as shown in FIG. 2D. The chemical release occurs only from the exposed face(s) 14 whose surface area dictates the rate of release of chemical. Throughout the dissolution process, the surface area of the dissolution front is constant in these geometrical shapes and therefore the release substantially approximates zero-order kinetics. Because the exposed face(s) are in immediate contact with the fluid medium, the active ingredient is released immediately no lag time is observed. The volume of the core can be increased or decreased to accommodate different quantities of the active ingredient and excipients. The release rate, however, will be determined by the rate of erosion of the exposed surfaces and will be zero-order as long as the exposed surface of a dissolution device, or the ratio of the dissolution front to the diffusion path in a diffusion device, is constant. Another advantage of the present invention is the complete release of the active ingredient followed by the disintegration of remaining inert components of the delivery device. This is in contrast to many diffusion-based matrices, which leave a "ghost residue".

The invention is not restricted to cubical, rectangular and cylindrical objects. As depicted in FIG. 1, a variety of prismatic solids afford geometries in which exposed surfaces can dissolve without altering the surface area of the exposed face and are, therefore, considered to be within the scope of the current invention. This system has the advantage over other oral delivery systems that the chemical release profile can be easily modulated in a predictable manner simply by changing the geometrical configuration of its core thereby altering the exposed surface area of the shaped core. The amount of chemical compound(s) included in the core of the device will depend on the application for which it is being used, for example in the case of a therapeutically active compound, the amount will depend on the amount of chemical that is required to be delivered to the patient. Quantities of the therapeutically active compounds required to produce a pharmacological effect are well know to those skilled in the formulation art.

Impermeable coatings are common elements in many formulations. Impermeable coatings add mechanical strength and stability to the dosage form. They are also barriers which restrict contact between the external medium and the active ingredient and permit controlled release of the active material into the medium. Problems exist with presently available coatings. After active ingredient is released the remaining plastic coating may be excreted substantially unchanged which is unnecessary and objectionable. The mechanical properties of coatings vary and traditional spray coated polymers produces a polymeric film subject to stretching and cracking which allows shaped core to separate from the coating prior to complete release of the active ingredient. The present invention uses compression coating techniques to produce coatings with increased mechanical strength. The compression coating is optionally applied with a pore-forming material(s) which dissolve, leach or erode out of the polymer coat after delivery of the active compound is complete which introduces mechanical instability and the device and coating disintegrates or dissolves and is not excreted intact. The pores do not alter the release rate of the active ingredient.

Figure 3:
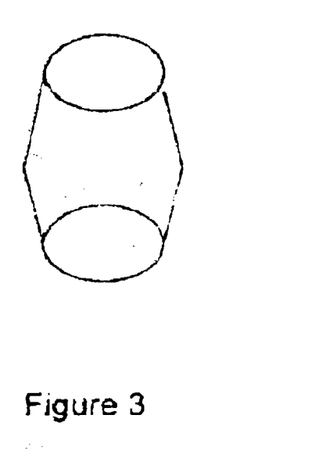
FIG. 3 illustrates an embodiment of the invention where the core is two frustums of a cone that are joined at the larger base. This geometry results in increasing quantities of drug delivered per unit time throughout the release period in a dissolution device or zero-order delivery from a diffusion device.
Figure 4:
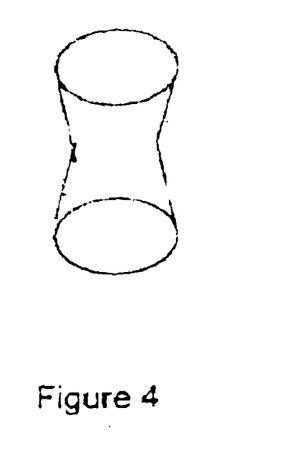
FIG. 4 illustrates an embodiment of the invention where the core is two frustums of a cone that are joined at the smaller base. This geometry results in decreasing quantities of drug delivered per unit time throughout the release period in a dissolution device or a diffusion device.
Figure 5A:
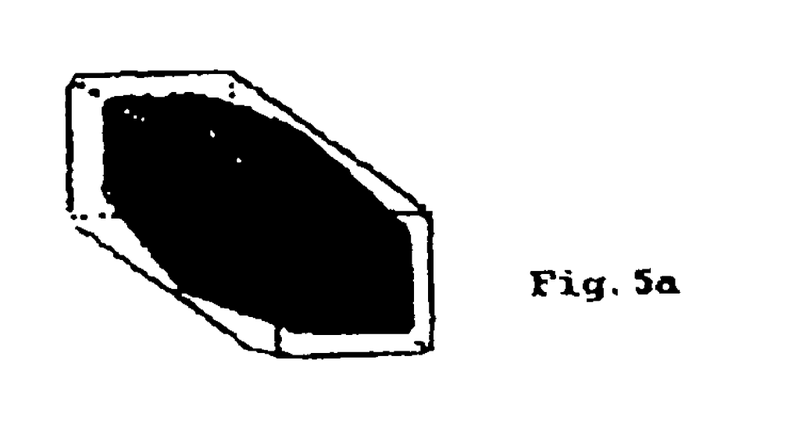
FIG. 5a illustrates an embodiment of the invention where the core is a truncated bipyramid. This geometry results in increasing quantities of drug delivered per unit time throughout the release period in a dissolution device or zero-order delivery from a diffusion device.
Figure 5B:
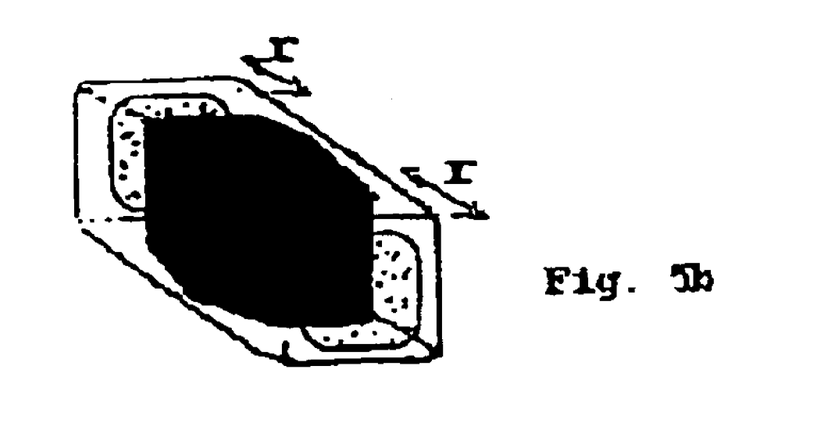
FIGS. 5b and 5c show the core at various stages of the release process.
Figure 5C:
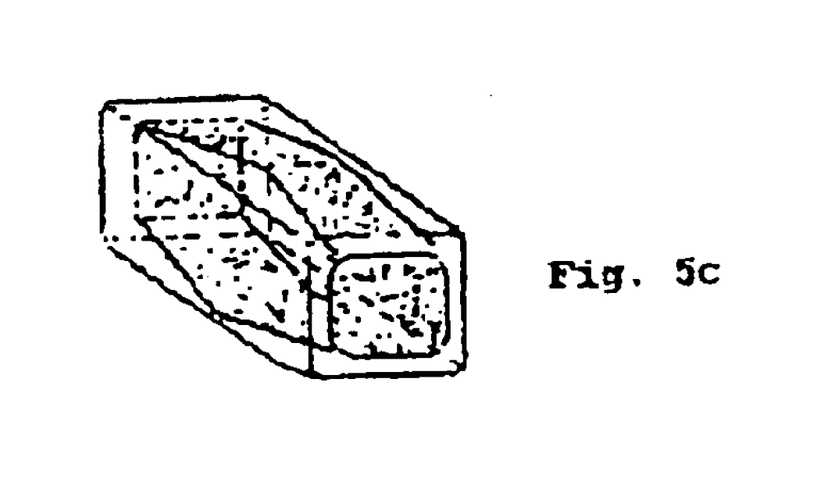
Figure 6:
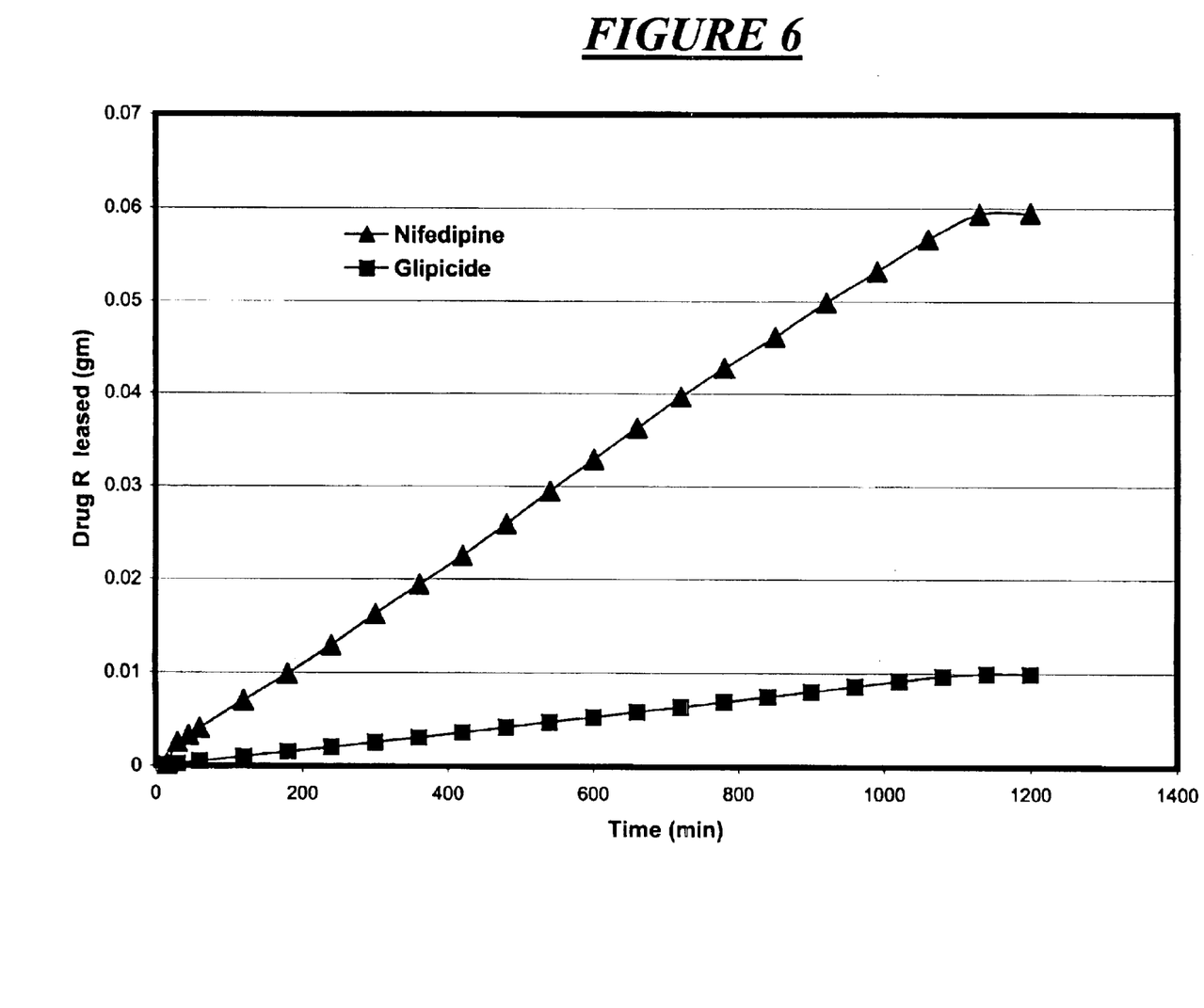
FIG. 6 illustrates the release profile of a zero-order sustained release of nifedipine and glipizide tablets from a device with a shaped core coated with a slowly disintegrating coating.

In another embodiment of the present invention the dissolution- or diffusion-controlled delivery device consists of a truncated bipyramid core (FIG. 5) or a two frustums of a cone joined at either the larger base (FIG. 3) or the smaller base (FIG. 4). In a dissolution-controlled release device, the surface area of the exposed face(s) in these geometries varies throughout the drug delivery resulting in a variable release rate. Altering the shape of the core to produce the desired surface profile permits the release profile of the active compound to be modified in an easily controlled fashion. According to Equation 1 the release rate of the active ingredient is proportional to the surface area of the exposed faces. In this embodiment that surface area either increases or decreases during the delivery period which results in a corresponding increase or decrease in the rate of drug release. The core geometries in FIGS. 3 and 5 result in increasing release rates during the release period whereas the release rate from the geometry in FIG. 4 decreases during the release period. One skilled in the art would recognize alternative shapes which would be equally effective and are considered part of the present invention. In this embodiment of the invention the core is again initially coated with an insoluble polymer containing a pore-forming material to limit exposure of the core to the medium during release of the active ingredient and to introduce mechanical instability into the coating after release of the active substance is completed.

In yet another embodiment of the present invention there is provided a diffusion delivery device. In contrast to dissolution devices, the geometries depicted in FIGS. 3 and 5 produce a substantially constant release rate in a diffusion-controlled device. The diffusion device is particularly effective for delivering water soluble ingredients and typically comprises a compressed core containing the active ingredient and an insoluble matrix. The surface area of the dissolution front and the diffusion path length vary throughout the delivery period and the dependence of the release rate on the area of the dissolution front is given by Equation 2. This embodiment of the invention the core is also coated with an insoluble polymer containing a pore-forming material. The insoluble matrix in a diffusion release device leaves a depleted ghost residue which will be voided intact unless means for disintegration are incorporated into the device. Dissolution or disintegration of the coating permits the insoluble structural elements to disintegrate.

Still another embodiment of the present invention provides for zero-order release of the active ingredient from a geometrically shaped core that is comprised of less than 90% of a therapeutic compound. The core is surrounded by a coating comprising an insoluble or slowly soluble polymer and, optionally, a soluble component which leaches out of the coat rendering it porous, weak and susceptible to disintegration shortly after release of the active ingredient is complete. Earlier devices disclosed cores comprised of greater than 90% of the active component; however, such cores afford limited opportunity to control the release rate. Hydrophilic drugs require the presence of dissolution regulators to prevent rapid and immediate dissolution of the entire core. This embodiment allows the release rate to be optimized for different active ingredients. The core coating remains intact throughout the delivery period but disintegrates prior to evacuation from the colon.

Examples of some chemical compounds that may be used include, but are not limited to, therapeutically active compounds, active compounds used in insecticides, active compounds used in pesticides, and active compounds used in water treatments in swimming pools and toilets, and other applications in which the release of a chemical or chemicals is required at a controlled rate. Examples of some chemical compounds that may be used include, but are not limited to, inorganic and organic pharmaceutical agents such as psychotherapeutic agents, anti-diabetic drugs, anticonvulsants, cardiovascular drugs, stroke treatment agents, respiratory therapies, anti-infective agents, migraine therapies, urinary tract agents, contraceptives, analgesics, cholesterol reducers, anti-arthritic agents, gastrointestinal products, muscle-relaxants, muscle-contractants, anti-Parkinson agents, anti-inflammatory agents, hormonal agents, diuretics, and electrolytes. Examples of drugs that can be formulated into the dissolution based or diffusion based device include aspirin, bupropion hydrochloride, buspirone hydrochloride, carbamazepine, carbidopa, cephalosporin, cimetidine hydrochloride, citalopram hydrobromide, clarithromycin, clonidine, diclofenac sodium, diltiazem hydrochloride, dipyridamole, divalproex sodium, doxazosin mesylate, enalapril maleate, ethinyl estradiol, etodolac, fexofenadine hydrochloride, glipizide, haloperidol, ibuprofen, indomethacin, isosorbide dinitrate, isosorbide mononitrate, isradipine, ketoprofen, labetalol, lansoprazole, levodopa, lithium carbonate, loratidine, lovastatin, methascopolomine chloride, metformin hydrochloride, metronidazole, methylphenidate hydrochloride, metoprolol succinate, morphine sulfate, naproxen sodium, nifedipine, nisoldipine, norethindrone acetate, omeprazole, oxybutynin chloride, oxycodone hydrochloride, penicillin, pentoxifylline, potassium chloride, pseudoephedrine hydrochloride, rabeprazole sodium, ranitidine hydrochloride, salbutamol, terfenadine, theophylline, tramadol hydrochloride, trandolapril, venlafaxine hydrochloride, verapamil hydrochloride, and the like, and alternative or pharmaceutically acceptable salts thereof.

Examples of polymers that are either soluble polymers or polymers that produce clear colloidal dispersion in water that may be used include, but are not limited to: hydroxypropyl cellulose, hydroxyethyl cellulose, hydroxypropyl methylcellulose; polyvinylpyrrolidone, methyl cellulose, soluble modified starches, gelatin, acacia, polyethyleneoxide, and polyethyleneglycol. Water insoluble polymers that may be used, but are not limited to, include: cellulose acetate, cellulose acetate butyrate, polyvinyl alcohol, ethyl cellulose, methacrylic acid copolymers, insoluble modified starches, and polypropylene oxide. Biodegradable polymers that may be used include: polyglycolide, poly-L-lactide, poly-D,L-lactide, caprolactone, polyamino acids, polyorthoesters and polyanhydrides. One skilled in the art will recognize other polymers with similar properties which also may be used and the invention is not limited to the specific polymers listed above.

Examples of suitable pore-forming materials include, but are not limited to, alkali and alkaline earth metal salts, organic compounds such as polysaccharides, organic aliphatic alcohols including diols, polyols; polyhydric alcohol, polyalkylene glycol, polyglycol, $\alpha,\omega$-alkylenediols, and the like. The pore-forming elements can have a size of about 0.1 to 200 microns. In a presently preferred embodiment, the means or wall comprises 1 to 50% of pore former based on the weight of the polymer. Preferred pore-forming materials include sugars, e.g., dextrose, fructose, glucose, dextrates, sorbitol, propylene glycol, glycerin and carbowax.

Examples of suitable soluble diluents that may be incorporated into the core include, but are not limited to, lactose, sucrose, carbowax, dextrates, glucose, fructose, soluble starch, sorbitol, mannitol, hydroxypropyl cellulose, hydroxyethyl cellulose, hydroxypropyl methylcellulose, polyvinylpyrrolidone, methyl cellulose, soluble modified starches, gelatin, acacia. Examples of biodegradable diluents that may be incorporated into the core include, but are not limited to, polyglycolide, poly-L-lactide, poly-D,L-lactide, caprolactone, polyamino acids, polyorthoesters, and polyanhydrides. Examples of pH sensitive diluents diluents include cellulose acetate phthalate, hydroxypropyl methylcellulose phthalate, polyvinylacetate phthalate and polymethacrylate. Examples of suitable insoluble diluents that may be used include, but are not limited to, calcium sulfate, dicalcium phosphate, microcrystalline cellulose, insoluble modified starches and starch.

Examples of suitable lubricants that may be used include, but are not limited to, stearic acid, sodium stearate, calcium stearate, magnesium stearate and sodium lauryl sulfate.

Yet another embodiment of the current invention further provides a process for manufacturing the chemical delivery device. The manufacturing process comprises the steps of forming a mixture of at least one chemical compound and at least one rate modifier, and then compressing the mixture into a geometrically shaped core comprising at least one exposed face. The process further includes coating the shaped core with an inactive coat, the coat covering all the faces of the core except at least one exposed face. In one embodiment of the invention the shaped core is scored to assist in securing the coating to the core.

The dissolution-based cores are composed primarily of soluble excipients whereas diffusion based cores may contain soluble and insoluble excipients. Granules for the bodies are prepared using conventional, dry or wet granulation methods and the bodies are compressed on a conventional press. No special tooling is required in this system for the compression of the active core.

A dry process does not require the use of solvents for the compression coating. Coating formulations for both diffusion and dissolution-based systems are composed of insoluble pharmaceutically acceptable polymers and soluble plasticizers or soluble compounds. Granules for coating may be prepared either by dry granulation or wet granulation method.

The pre-compressed bodies are then compression coated using a core-coater fitted with a specially designed tooling for placing bodies precisely in the dyes. Approximately fifty percent of the required coating material is transferred to the die and the core is placed precisely at the desired location on the top of the granules in the die. The remaining fifty-percent of the coating granules are then placed on top of the core. The punches are then brought closer together to compress all the components of the device. An example of a suitable core-coater is manufactured by Korsche Pressing. Any machine can be used that allows the geometrically shaped core to be coated, preferably a machine that uses a device to pick up the bodies for the precise placement in the center of the dye.

Although specific methods for manufacturing the chemical delivery devices are described below, numerous modifications and alternative process steps will be apparent to those skilled in the art. Accordingly, this description is to be construed as illustrative only and is for the purpose of teaching those skilled in the art methods to prepare the invention. These processes may be varied substantially without departing from the spirit of the invention and the exclusive use of all modifications which come within the scope of the appended claim is reserved.

EXAMPLE 1

Dry Granulation Method for Core Compression

In an appropriate blender, the chemical is blended with a dissolution regulator which comprise the dissolution-based core. If required a soluble or insoluble diluent may also be added. Suitable polymers and diluents are known in the art and examples are described above. The blend may be milled and sieved, if desired, through a sieve with an appropriate size mesh, the mesh size is chosen according to the application. The blend is then mixed with a lubricant and the lubricated blend is compressed on a conventional rotary or single punch machine, examples of which are known in the art, into a tablet core of the appropriate shape and size.

EXAMPLE 2

Wet Granulation Method for Core Compression

In an appropriate blender, the chemical is blended with either a slow dissolving polymer—which comprise the shaped core. If required a soluble or insoluble diluent may also be added. The blend is subsequently granulated with water or an organic solvent or a mixture of water and an organic solvent. Alternatively a slow dissolving or dispersing polymer may be dissolved or dispersed in a solvent and added to the blend while mixing continuously. The mixture thus granulated is then dried at a suitable temperature and milled through a screen with an appropriate opening. The granules prepared are then mixed with a soluble or insoluble lubricant. The lubricated granules are compressed into a tablet core of the appropriate shape. Examples of suitable core compressing machines that may be used are known in the art and supplied by, for example Killian & Co. Inc. (Pennsylvania, USA), Thomas Engineering (Illinois, USA) and Fette America Inc. (New Jersey, USA).

EXAMPLE 3

Dry Granulation Method for Coating

An insoluble polymer and optionally a pore-former and/or a plasticizer are mixed in a suitable blender, and then the blend may be milled through a screen with an appropriate size mesh. The milled blend is lubricated with a soluble or insoluble lubricant. The core is covered with the blend and the coating applied by compression.

EXAMPLE 4

Wet Method for Coating

An insoluble polymer and optionally a pore-former and/or a plasticizer are blended together, and then the blend may be milled through a screen with appropriate size mesh. The blended material is granulated with a solution of a polymer in water. The granules are dried at a suitable temperature and screened through a mesh of appropriate size. The coating blend is lubricated with a soluble or insoluble lubricant. The core is covered with the blend and the coating applied by compression.

EXAMPLE 5

Nifedipine Tablets

Nifedipine (60 g.), lactose monohydrate (112.5 g.) and hydroxypropyl methylcellulose 5 cps (124.5 g.) were blended in a Diosna High Speed Blender for 2 min and sized through a 20 mesh screen. The blend was granulated with water and dried at 60° C. and then milled through a 20 mesh screen. The milled material was lubricated with magnesium stearate (3 g.). The lubricated blend was compressed under a compression force of 23 kilonewtons into a 10 mm diameter and 6 mm thick cylindrical core weighing 300 mg. All but two surfaces of the core were compression coated with a blend of 50 g methacrylate S-100, 50 g methacrylate RSPO and 7.5g triethylcitrate and 5 g fine sorbitol. The coated tablets were heated at 80° C. for one hour.

EXAMPLE 6

Glipizide Tablets

Glipizide(8 g.), lactose monohydrate (95 g.) and hydroxypropyl methylcellulose 5 cps (95 g.) were blended in a high speed blender and sized through a 20 mesh screen. The blend was granulated with water, dried at 60° C. and then milled through a 20 mesh screen. The milled material was lubricated with sodium stearate 2 g.). The lubricated blend was compressed into a 4×4×10 mm rectangular core weighing 250 mg. All but two surfaces of the core were compression coated with a blend of 25 g cellulose acetate, 65 g ethyl cellulose and 6 g dextrate, 3 g ethyl lactate and 1 g fine magnesium stearate. The coated tablets were heated at 80° C. for one hour. The total weight after coating is 500 mg.

EXAMPLE 7

Nifedipine and Glipizide Release Profiles

The release profile of nifedipine and glipizide were determine in simulated gastric fluid containing 1% sodium lauryl sulfate using apparatus 2 described in the U.S. Pharmacopeia <XXIV> incorporated herein by reference. The data is depicted in FIG. 3. Nifedipine and glipizide were completely release in 20 and 19 hours respectively. The release rates and correlation coefficient for the data for both nifedipine and glipizide were 3.13 mg/hr (0.99858) and 0.528 mg/hr (0.99882) respectively. Both compounds exhibited constant first order release.

Although this invention has been described with reference to specific embodiments thereof, it is understood that other embodiments and variations of the invention as described and exemplified may be made by those skilled in the art without departing from the true spirit of the invention. It is intended that the appended claims be construed to include all such embodiments and variations.

I claim:

1. A dissolution-controlled chemical delivery device providing substantially controlled-release of at least one active ingredient into a gastrointestinal fluid throughout a substantial portion of a delivery period which composition comprises:

(i) a shaped core (a) having at least one planar dissolution-controlled release face, (b) comprising a compressed mixture containing less than 90% (w/w) of the active ingredient homogeneously mixed with at least one dissolution regulator operable to release the active ingredient from said release face wherein a release rate is determined by a surface area and rate of erosion of the release face, and optionally (c) having a score circumscribed on the surface to secure a coating;

(ii) a mechanically strong granule compression coating surrounding and adhering to said core except the release face(s), said coating comprising an insoluble polymer selected from the group consisting of ethyl cellulose, cellulose acetate, cellulose acetate butyrate, polyvinyl alcohol, polyvinyl acetate and a methacrylic acid copolymer, optionally at least one pore-forming element, and at least one pH sensitive element selected from the group consisting of cellulose acetate phthalate, hydroxypropyl methylcellulose phthalate, polyvinylacetate phthalate and polymethacrylate operable to permit disintegration of the coating after release of said active ingredient is completed, wherein said coating does not alter a release rate of the active ingredient.

2. A device according to claim 1 wherein said device is rectangular and said planar release surface is square or rectangular.

3. A device according to claim 1 wherein said core is a cylinder and said planar release face is circular.

4. A device according to claim 1 wherein said core is a prism and said planar release surface is a polygon.

5. A device according to claim 1 wherein said core has two exposed planar release surfaces.

6. A method of delivering an active ingredient with a constant controlled release of an active compound into a gastrointestinal fluid comprising: (a.) incorporating at least one biologically active ingredient into a tablet having: (i) a shaped core (a) having at least one planar release face wherein the area of the dissolution surface of said surface increases throughout the delivery period to compensate for an increase in the diffusion path length and (b) a compressed mixture of the biologically active ingredient homogeneously mixed with at least one insoluble polymer operable to release the biologically active ingredient from said exposed surface; (ii) a mechanically strong granule compression coating surrounding and adhering to said core except the release face(s), said coating comprising an insoluble polymer selected from the group consisting of ethyl cellulose, cellulose acetate, cellulose acetate butyrate, polyvinyl alcohol, polyvinyl acetate and a methacrylic acid copolymer, and optionally at least one pore-forming element, and at least one pH sensitive element selected from the group consisting of cellulose acetate phthalate, hydroxypropyl methylcellulose phthalate, polyvinylacetate phthalate and polymethacrylate operable to permit disintegration of the coating after release of said active ingredient is completed, wherein said coating does not alter a release rate of the active ingredient, and said coating disintegrating over a substantially longer period of time than is required for said dissolution regulator to release said biologically active ingredient; and, (b) placing said tablet in a fluid medium in need of the presence of said active ingredient.

7. A device according to claim 1 wherein said pore-forming element(s) is selected form a group consisting of dextrose, fructose, glucose, dextrates, sorbitol, propylene glycol, glycerin and carbowax.

8. A device according to claim 1 wherein said dissolution regulator is selected from a group consisting of hydroxypropyl cellulose, hydroxyethyl cellulose, hydroxypropyl methylcellulose, polyvinylpyrrolidone, methyl cellulose, soluble modified starches, gelatin, and acacia.

9. A device according to claim 1 where said active ingredient is a pharmaceutical agent for human use.

10. A device according to claim 9 where said active ingredient is selected from a group consisting of psychotherapeutic agents, anti-diabetic drugs, anticonvulsants, cardiovascular drugs, stroke treatment agents, respiratory therapies, anti-infective agents, migraine therapies, urinary tract agents, contraceptives, analgesics, cholesterol reducers, anti-arthritic agents, gastrointestinal products, muscle-relaxants, muscle-contractants, anti-Parkinson agents, anti-inflammatory agents, hormonal agents, diuretics, electrolytes, serotonin agonists and antagonists.

11. A device according to claim 9 where said active ingredient is selected from a group consisting of aspirin, bupropion hydrochloride, buspirone hydrochloride, carbamazepine, carbidopa, cephalosporin, cimetidine hydrochloride, citalopram hydrobromide, clarithromycin, clonidine, diclofenac sodium, diltiazem hydrochloride, dipyridamole, divalproex sodium, doxazosin mesylate, enalapril maleate, ethinyl estradiol, etodolac, fexofenadine hydrochloride, glipizide, haloperidol, ibuprofen, indomethacin, isosorbide dinitrate, isradipine, ketoprofen, labetalol, lansoprazole, levodopa, lithium carbonate, loratidine, lovastatin, methascopolomine chloride, metformin hydrochloride, metronidazole, methylphenidate hydrochloride, metoprolol succinate, morphine sulfate, naproxen sodium, nifedipine, nisoldipine, norethindrone acetate, omeprazole, oxybutynin chloride, oxycodone hydrochloride, penicillin, pentoxifylline, potassium chloride, pseudoephedrine hydrochloride, rabeprazole sodium, ranitidine hydrochloride, salbutamol, terfenadine, theophylline, tramadol hydrochloride, trandolapril, venlafaxine hydrochloride, verapamil hydrochloride, and pharmaceutically acceptable salts thereof.

12. A method of delivering a substantially constant controlled release of an active compound into a gastrointestinal fluid comprising: (a) incorporating at least one biologically active ingredient into a tablet having: (i) a shaped core (a) having at least one planar dissolution-controlled release face wherein the dimensions of said face remain constant throughout a substantial portion of the delivery period, and (b) comprising a compressed mixture of the biologically active ingredient homogeneously mixed with at least one dissolution regulator operable to release the biologically active ingredient from said release face, and optionally (c) having a score circumscribed on the surface to secure the coating; (ii) a mechanically strong granule compression coating surrounding and adhering to said core except the release face(s), said coating comprising an insoluble polymer selected from the group consisting of ethyl cellulose, cellulose acetate, cellulose acetate butyrate, polyvinyl alcohol, polyvinyl acetate and a methacrylic acid copolymer, optionally at least one pore-forming element, and at least one pH sensitive element selected from the group consisting of cellulose acetate phthalate, hydroxypropyl methylcellulose phthalate, polyvinylacetate phthalate and polymethacrylate operable to permit disintegration of the coating after release of said active ingredient is completed, wherein said coating does not alter a release rate of the active ingredient, and said coating disintegrating over a substantially longer period of time than is required for said dissolution regulator to release said biologically active ingredient; and, (b) placing said tablet in a fluid medium in need of the presence of said active ingredient.

13. A dissolution-controlled chemical delivery device providing controlled variable release of at least one biologically active ingredient into a gastrointestinal fluid throughout a substantial portion of the delivery period which composition comprises (i) a shaped core (a) having at least one planar dissolution-controlled release face wherein the dissolution of said face causes at least one of the dimensions of said face to vary thereby increasing or decreasing the surface area of said face throughout a substantial portion of the delivery period, and (b) the biologically active ingredient homogeneously mixed with at least one dissolution regulator operable to release the biologically active ingredient from said release face, and; (ii) a mechanically strong granule compression coating surrounding and adhering to said core except the release face(s), said coating comprising an insoluble polymer selected from the group consisting of ethyl cellulose, cellulose acetate, cellulose acetate butyrate, polyvinyl alcohol, polyvinyl acetate and a methacrylic acid copolymer, optionally at least one pore-forming element, and at least one pH sensitive element selected from the group consisting of cellulose acetate phthalate, hydroxypropyl methylcellulose phthalate, polyvinylacetate phthalate and polymethacrylate operable to permit disintegration of the coating after release of said active ingredient is completed, wherein said coating does not alter a release rate of the active ingredient.

14. A device according to claim 13 wherein said core is a truncated bipyramid and said planar release face is a square.

15. A device according to claim 13 wherein said device is two frustums of a cone said frustums being attached at either base wherein said release surface is circular.

16. A device according to claim 13 wherein said pore-forming element is selected form a group consisting of dextrose, fructose, glucose, dextrates, sorbitol and carbowax.

17. A device according to claim 13 wherein said dissolution regulator is selected from a group consisting of hydroxypropyl cellulose, hydroxyethyl cellulose, hydroxypropyl methylcellulose, polyvinylpyrrolidone, methyl cellulose, soluble modified starches, gelatin, and acacia.

18. A device according to claim 13 where the active ingredient is a pharmaceutical agent for human use.

19. A device according to claim 18 where the active ingredient is selected from a group consisting of psychotherapeutic agents, antidiabetic drugs, anticonvulsants, cardiovascular drugs, stroke treatment agents, respiratory therapies, anti-infective agents, migraine therapies, urinary tract agents, contraceptives, analgesics, cholesterol reducers, antiarthritic agents, gastrointestinal products, muscle-relaxants, muscle-contractants, anti-Parkinson agents, anti-inflammatory agents, hormonal agents, diuretics, electrolytes, serotonin agonists and antagonists.

20. A device according to claim 18 where the active ingredient is selected based on a suitable half-life and adsorption characteristics from a group consisting of aspirin, bupropion hydrochloride, buspirone hydrochloride, carbamazepine, carbidopa, cephalosporin, cimetidine hydrochloride, citalopram hydrobromide, clarithromycin, clonidine, diclofenac sodium, diltiazem hydrochloride, dipyridamole, divalproex sodium, doxazosin mesylate, enalapril maleate, ethinyl estradiol, etodolac, fexofenadine hydrochloride, glipizide, haloperidol, ibuprofen, indomethacine, isosorbide dinitrate, isradipine, ketoprofen, labetalol, lansoprazole, levodopa, lithium carbonate, loratidine, lovastatin, methascopolomine chloride, metformin hydrochloride, metronidazole, methylphenidate hydrochloride, metoprolol succinate, morphine sulfate, naproxen sodium, nifedipine, nisoldipine, norethindrone acetate, omeprazole, oxybutynin chloride, oxycodone hydrochloride, penicillin, pentoxifylline, potassium chloride, pseudoephedrine hydrochloride, rabeprazole sodium, ranitidine hydrochloride, salbutamol, terfenadine, theophylline, tramadol hydrochloride, trandolapril, venlafaxine hydrochloride, verapamil hydrochloride, and pharmaceutically acceptable salts thereof.

21. A method of delivering an active ingredient with a controlled variable release of an active compound into a gastrointestinal fluid comprising: (a.) incorporating at least one biologically active ingredient into a tablet having: (i) a shaped core (a) having at least one planar dissolution-controlled release face wherein the dissolution of said face causes at least one of the dimensions of said face to vary thereby increasing or decreasing the surface area of said face throughout a substantial portion of the delivery period, and (b) a compressed mixture of the biologically active ingredient homogeneously mixed with at least one dissolution regulator operable to release the biologically active ingredient from said release face; and, (ii) a mechanically strong granule compression coating surrounding and adhering to said core except the release face(s), said coating comprising an insoluble polymer selected from the group consisting of ethyl cellulose, cellulose acetate, cellulose acetate butyrate, polyvinyl alcohol, polyvinyl acetate and a methacrylic acid copolymer, optionally at least one pore-forming element, and at least one pH sensitive element selected from the group consisting of cellulose acetate phthalate, hydroxypropyl methylcellulose phthalate, polyvinylacetate phthalate and polymethacrylate operable to permit disintegration of the coating after release of said active ingredient is completed, wherein said coating does not alter a release rate of the active ingredient, and said coating disintegrating over a substantially longer period of time than is required for said dissolution regulator to release said biologically active ingredient; and, (b) placing said tablet in a fluid medium in need of the presence of said active ingredient.

22. A diffusion-controlled chemical delivery device providing substantially constant-controlled-release of at least one active ingredient into a gastrointestinal fluid throughout a substantial portion of the delivery period which composition comprises: (i) a shaped core having (a) at least one planar release face wherein the dimensions of said face remain constant throughout a substantial portion of the delivery period, and (b) a planar dissolution surface within the matrix wherein the surface area of said dissolution surface increases throughout the delivery period to compensate for an increase in the diffusion path length, and, comprising (c) a compressed mixture containing less then 90% (w/w) of the active ingredient homogeneously mixed with at least one component insoluble in the fluid media operable to release the active ingredient from said release face; and, (ii) a mechanically strong granule compression coating surrounding and adhering to said core except the release face(s), said coating comprising an insoluble polymer selected from the group consisting of ethyl cellulose, cellulose acetate, cellulose acetate butyrate, polyvinyl alcohol polyvinyl acetate and a methacrylic acid copolymer, optionally at least one pore-forming element, and at least one pH sensitive element selected from the group consisting of cellulose acetate phthalate, hydroxypropyl methylcellulose phthalate, polyvinylacetate phthalate and polymethacrylate operable to permit disintegration of the coating after release of said active ingredient is completed.

23. A device according to claim 22 wherein said core is a truncated bipyramid and said planar release face is a square.

24. A device according to claim 22 wherein said device is a truncated bipyramid wherein said planar release surface is circular.

25. A device according to claim 22 where said active ingredient is a pharmaceutical agent for human use.

26. A device according to claim 22 where said active ingredient is selected from a group consisting of psychotherapeutic agents, anti-diabetic drugs, anticonvulsants, cardiovascular drugs, stroke treatment agents, respiratory therapies, anti-infective agents, migraine therapies, urinary tract agents, contraceptives, analgesics, cholesterol reducers, anti-arthritic agents, gastrointestinal products, muscle-relaxants, muscle-contractants, anti-Parkinson agents, anti-inflammatory agents, hormonal agents, diuretics, electrolytes, serotonin agonists and antagonists.

27. A device according to claim 22 where the pharmaceutical active is selected from a group consisting of aspirin, bupropion hydrochloride, buspirone hydrochloride, carbamazepine, carbidopa, cephalosporin, cimetidine hydrochloride, citalopram hydrobromide, clarithromycin, clonidine, diclofenac sodium, diltiazem hydrochloride, dipyridamole, divalproex sodium, doxazosin mesylate, enalapril maleate, ethinyl estradiol, etodolac, fexofenadine hydrochloride, glipizide, haloperidol, ibuprofen, indomethacine, isosorbide dinitrate, isradipine, ketoprofen, labetalol, lansoprazole, levodopa, lithium carbonate, loratidine, lovastatin, methascopolomine chloride, metformin hydrochloride, metronidazole, methylphenidate hydrochloride, metoprolol succinate, morphine sulfate, naproxen sodium, nifedipine, nisoldipine, norethindrone acetate, omeprazole, oxybutynin chloride, oxycodone hydrochloride, penicillin, pentoxifylline, potassium chloride, pseudoephedrine hydrochloride, rabeprazole sodium, ranitidine hydrochloride, salbutamol, terfenadine, theophylline, tramadol hydrochloride, trandolapril, venlafaxine hydrochloride, verapamil hydrochloride, and alternative or pharmaceutically acceptable salts thereof.

\* \* \* \* \*